(12) United States Patent
Jo et al.

(10) Patent No.: US 11,123,163 B2
(45) Date of Patent: Sep. 21, 2021

(54) CUSTOM DENTAL MEMBRANE

(71) Applicant: DENTSPLY SIRONA Inc., York, PA (US)

(72) Inventors: Jeremy E. Jo, Somerville, MA (US); Jennifer DiPietro, North Easton, MA (US)

(73) Assignee: DENTSPLY SIRONA INC., York, PA (US)

( * ) Notice: Subject to any disclaimer, the term of this patent is extended or adjusted under 35 U.S.C. 154(b) by 217 days.

(21) Appl. No.: 16/374,962

(22) Filed: Apr. 4, 2019

(65) Prior Publication Data
US 2020/0315753 A1 Oct. 8, 2020

(51) Int. Cl.
*A61F 2/28* (2006.01)
*A61C 13/00* (2006.01)
*A61F 2/46* (2006.01)
*A61C 9/00* (2006.01)

(52) U.S. Cl.
CPC ...... *A61C 13/0004* (2013.01); *A61C 13/0019* (2013.01); *A61F 2/2846* (2013.01); *A61F 2/4601* (2013.01); *A61C 9/0053* (2013.01); *A61L 2430/12* (2013.01)

(58) Field of Classification Search
CPC .... A61F 2/4601; A61F 2/2846; A61F 2/3094; A61C 13/0019; A61C 13/0004; A61C 8/0006; A61C 9/0053; A61L 2430/12; A61B 5/05; G09B 23/283
See application file for complete search history.

(56) References Cited

U.S. PATENT DOCUMENTS

| | | | |
|---|---|---|---|
| 6,616,698 B2 | 9/2003 | Scarborough | |
| 7,531,004 B2 | 5/2009 | Bagga | |
| 9,433,707 B2 | 9/2016 | Swords | |
| 10,105,198 B2 | 10/2018 | Moon | |
| 2009/0262109 A1* | 10/2009 | Markowitz | A61B 5/068 345/419 |
| 2010/0215718 A1* | 8/2010 | Swords | A61L 27/227 424/423 |
| 2018/0303616 A1* | 10/2018 | Bhattacharyya | A61F 2/30942 |
| 2019/0038384 A1 | 2/2019 | Lizarazo | |
| 2020/0138518 A1* | 5/2020 | Lang | A61B 90/37 |

FOREIGN PATENT DOCUMENTS

| | | |
|---|---|---|
| DE | 10138373 A1 | 3/2003 |
| DE | 102017005036 A1 | 12/2017 |
| WO | 2009137947 A1 | 11/2009 |

OTHER PUBLICATIONS

International Search Report; PCT/US2020/024812; Jun. 8, 2020 (completed); dated Jun. 18, 2020.
Written Opinion of the International Searching Authority; PCT/US2020/024812; Jun. 8, 2020 (completed); dated Jun. 18, 2020.

* cited by examiner

*Primary Examiner* — Brian E Pellegrino
(74) *Attorney, Agent, or Firm* — Dentsply Sirona Inc.

(57) ABSTRACT

A method and system for making a preformed dental membrane using three-dimensional (3D) patient data. A patient jaw having insufficient bone at a surgical site may be scanned to provide a 3D image which may be used to design a virtual preformed dental membrane and fabricate for placement over packed bone graft substitute.

7 Claims, 6 Drawing Sheets

CUSTOM DENTAL MEMBRANE

FIELD OF THE INVENTION

The present application relates generally to a preformed dental membrane and more specifically to a custom dental membrane and a method and system for making the custom dental membrane using three-dimensional (3D) patient data.

BACKGROUD OF THE INVENTION

Natural teeth in humans may be supported in jawbone by periodontal fibers that function as shock absorbers when a compressive force is applied, such as during chewing. Due to tooth decay, accidental injury, anatomical abnormalities, age, and the like, a natural tooth of a patient may be removed or missing. As a result, dental implant devices may be implanted in the patient's bone structure to improve the patient's physical appearance and/or tooth function.

When teeth are removed or missing, bone that used to surround them may begin to resorb. Moreover, losing enough teeth and tooth-supporting bone, may cause facial features to sag, resulting in a more aged appearance. With bone grafting-techniques, bone that has been lost may be built up again, therefore benefiting a patient's health and/or appearance by strengthening their jawbone and allowing more effective tooth replacement.

During a bone grafting procedure, an incision may be made in the patient's gums to gain access to the bone beneath it, and then grafting material/bone graft substitute (BGS) may be added. The grafting material may be processed bone minerals around which the body may deposit new bone cells.

Currently, a dental professional may augment the patient's maxillary and mandibular ridge with the bone graft substitute (BGS) which may be available in a particle or block form, and the clinician may pack this material into areas where additional bone growth is required. This material may subsequently be covered with a porous membrane structure to act as a barrier from the soft tissue. The barrier may be required with bone grafts to ensure that the hard and soft tissue remain separate, so that soft tissue does not grow into the bone graft material.

Current membranes are commercially available in square or rectangular sheet formats. They may be delivered in sizes as small as 1×1 cm or as large as 3×4 cm or any permutation thereof.

During the use of a membrane, a clinician may first determine the size necessary for the grafting procedure, and then cut the membrane down to a size that best fits the patient's surgical site. Variables that determine this size may include the size of the graft site, the amount of membrane material use, the curvature of the dental anatomy, the direction or path of incision into the soft tissue, and/or the specific region of the graft location. The excess membrane may then be discarded after use.

These procedures may however be time consuming as the membranes come in standard shapes and a clinician has to cut each membrane down to a size and shape required for treating a patient.

U.S. Pat. No. 9,433,707B2 discloses biocompatible, non-resorbable porous containment structures for containment of bone graft material at a desired location for stimulation of bone growth. The porous containment structures may have interconnected pores sized to allow fibrovascular integration with surrounding tissue and conduction of vascular tissue through the structure into the bone graft material. It also discloses a method of facilitating growth of bone at a desired location by bending, a biocompatible, non-resorbable porous material comprising a porous matrix of interconnected pores into a shaped porous material for placement into the desired location, placing a bone graft material inside the interior region of the shaped porous material, placing the top portion in the closed position by bending the top portion relative to the side portion at the second shaped edge to cover the placed bone graft material, stably fixing the shaped porous material containing the bone graft material to structures adjacent to the desired location; and permitting bone to grow in the desired location.

U.S. Pat. No. 10,105,198B2 shows a dental membrane disposed in a deficient region of an alveolar bone to form a space for regeneration of the alveolar bone or to surround a bone graft, wherein the dental membrane is fixed by an insert inserted and fixed in the alveolar bone and a cover member combined to the insert, the dental membrane including: an upper portion surrounding a top surface of the deficient region of the alveolar bone; and a side bending portion bended downward from the upper portion and surrounding a side surface of the deficient region of the alveolar bone, wherein the upper portion includes: a combined portion combined to the insert and the cover member to be fixed; and a protruding portion extending and protruding upward from the combined portion.

U.S. Pat. No. 6,616,698B2 discloses an implantable, biocompatible, osteogenic bone graft that comprises at least one zone of impermeability to soft tissue ingrowth which is integral with the bone graft.

U.S. Pat. No. 7,531,004B2 discloses a pliable bone restorative having an osteoconductive foam that may at least partially surround a biocompatible mesh and wherein the foam comprises a biocompatible, resorbable polymer and calcium phosphate.

SUMMARY OF THE INVENTION

Existing limitations associated with the foregoing, as well as other limitations, may be overcome by a preformed dental membrane and a method and system for making the preformed dental membrane.

According to an aspect of the present invention a method may be provided for augmenting bone with bone graft substitute in a patient having inadequate bone quality or quantity, the method comprising the steps of: obtaining a virtual 3D image of an area of bone to be augmented, said area of bone to be augmented including a virtual representation of a surgical site; digitally packing the surgical site with virtual bone graft substitute; designing a virtual preformed dental membrane to be placed over the packed bone graft substitute based on the virtual bone graft substitute and the obtained virtual 3D image of the area of bone to be augmented; and fabricating a preformed dental membrane from the virtual preformed dental membrane.

According to another aspect of the present invention a method may be provided including one or more combinations of the following: (i) wherein the virtual 3D image of the area of bone to be augmented is obtained from a CBCT, MRI and/or intraoral scan, (ii) wherein the digital packing step is based on one or more properties selected from the group consisting of bone quality, region of graft, amount of graft, soft tissue topography, location of nerves, neighboring teeth or other critical dental anatomy, and location of the proposed dental implant (iii) further comprising; flattening the virtual preformed dental membrane into a substantially flat virtual sheet, (iv) further comprising physically packing the surgical site with bone graft substitute, (v) further comprising: placing the fabricated preformed membrane over the packed bone graft substitute such that when said fabricated preformed membrane is placed over the packed bone graft substitute, its geometry conforms or substantially conforms to that of said virtual preformed dental membrane, (vi) wherein the virtual 3D image of the area of bone to be augmented is obtained from a previous scanning operation.

Further features and advantages, as well as the structure and operation of various embodiments herein, are described in detail below with reference to the accompanying drawings.

BRIEF DESCRIPTION OF THE DRAWINGS

Example embodiments will become more fully understood from the detailed description given herein below and the accompanying drawings, wherein like elements are represented by like reference characters, which are given by way of illustration only and thus are not limitative of the example embodiments herein and wherein:

FIG. 2b illustrates a cross section of the rendering of FIG. 2a.

FIG. 4 illustrates perspective views of stages of creating a flattened preformed dental membrane from the graft shape of FIG. 2a.

Figure 1:
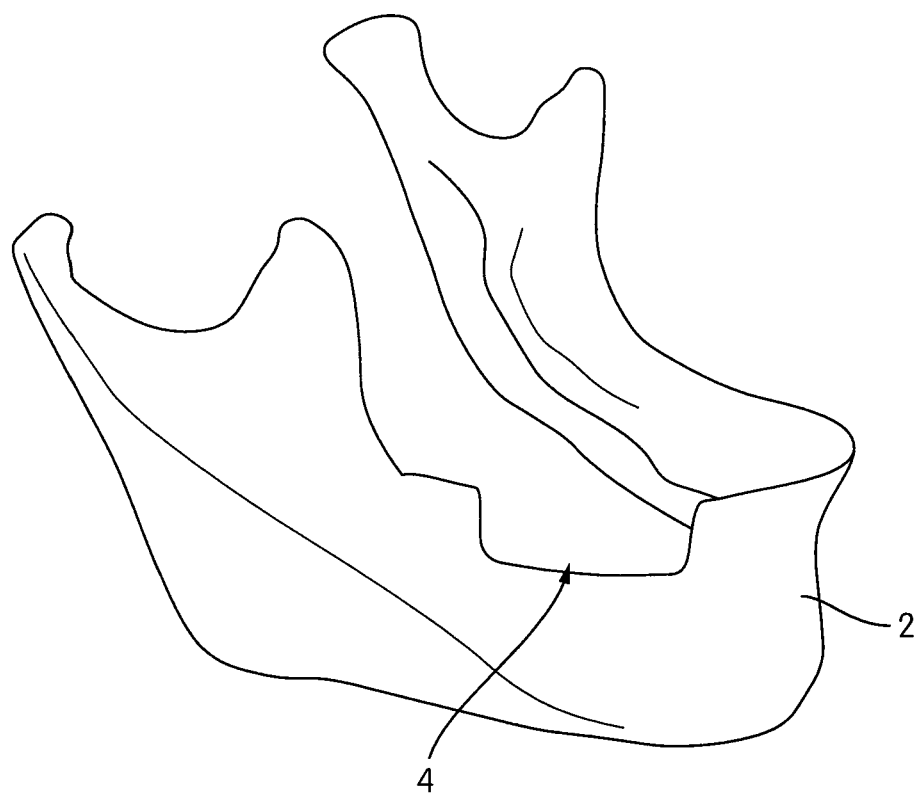
FIG. 1 illustrates a side view of a rendering of a jaw with insufficient bone for implant placement.

Different ones of the figures may have at least some reference numerals that may be the same in order to identify the same components, although a detailed description of each such component may not be provided below with respect to each Figure.

DETAILED DESCRIPTION OF THE INVENTION

Custom Dental Membrane and Method for Making Custom Dental Membrane.

In accordance with example aspects described herein, a custom/preformed dental membrane and a method for making the custom/preformed dental membrane that matches the shape of a surgical site may be realized.

Figure 2A:
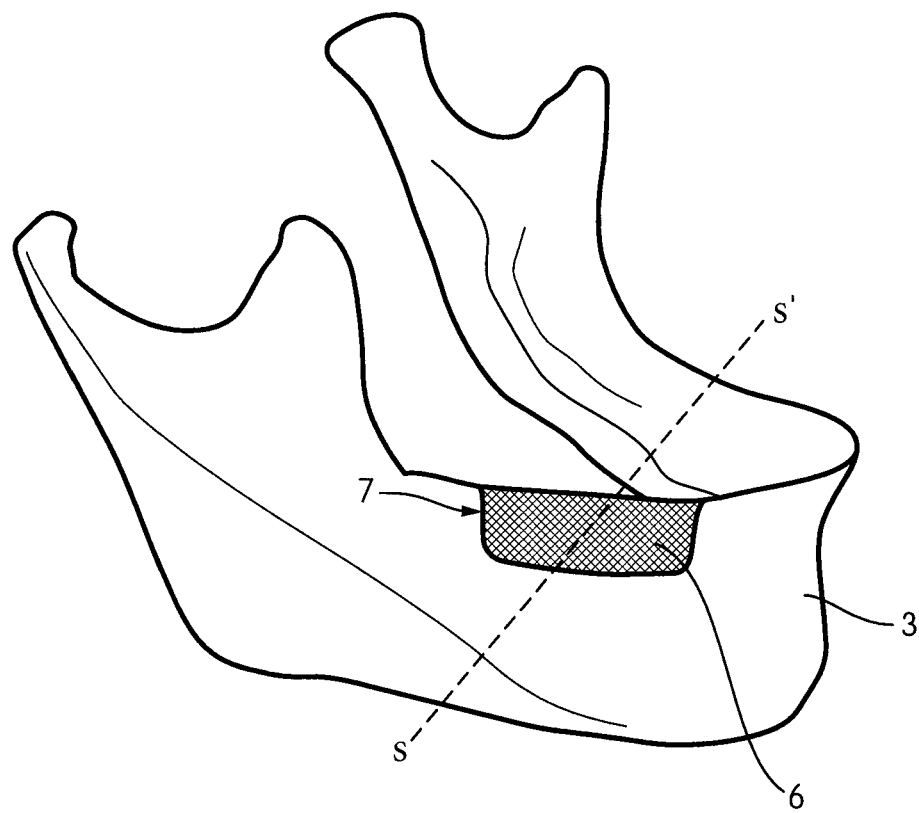
FIG. 2a illustrates a side view of the rendering of the jaw with a necessary amount of graft material to support a dental implant.
Figure 2B:
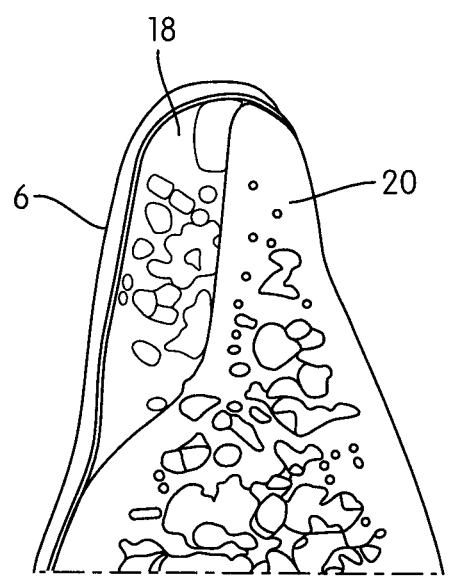

FIG. 1 shows a patient jaw 2 having insufficient bone at a surgical site 4. The insufficient bone in the patient jaw 2 may be due to factors such as periodontal disease, lost teeth, bone resorption, a thin maxillary and mandibular arch due to genetics, etc. By determining from a shape of the surgical site 4, from a virtual three-dimensional representation of the dental anatomy (such as a rendering of the jaw 3, shown in FIG. 2a) or a virtual three dimensional image of a portion or area of bone to be augmented, a virtual preformed membrane 6 may be produced to cover virtual bone graft substitute/material 18 placed in the surgical site 4 in order to separate hard tissue from soft tissue, so that soft tissue does not grow into the bone graft material. FIG. 2b shows a cross section along plane SS' of the rendering of the jaw 3, illustrating virtual bone graft substitute 18 packed alongside a thin section of bone 20. In an embodiment of the present invention, the rendering of the jaw 3 may be obtained by obtaining scan data may using cone beam or MRI and the scan data may be presented on screen in a digital file format such as dicom, stl, or some other format. The virtual preformed dental membrane 6 may be fabricated for use in a treatment procedure as discussed hereinafter.

In a preferred embodiment, a three dimensional image of an intended graft location/surgical site 4 or dental cavity may be obtained. This may be achieved by a number of methods, some of which may be discussed in further detail later. Use may be made of 3D image construction techniques such as, but not limited to, obtaining multiple two dimensional (2D) X-ray images at different orientations, and using computational techniques to convert these into a three dimensional image, using a Cone beam imaging device, a CAT-SCAN device, or some combination thereof. The 3D image of the dental cavity or surgical site may then be used a basis for producing a preformed dental membrane.

The physical preformed dental membrane may be molded or formed over a printed model of the augmented site. Herein, the physical preformed dental membrane may be made by using a 3D printer to print a negative form or mold, and the mold may then be used to produce the custom bone graft. In another embodiment, the membrane may be printed directly into its shape or printed directly on top of a printed bone graft substrate.

Figure 3:
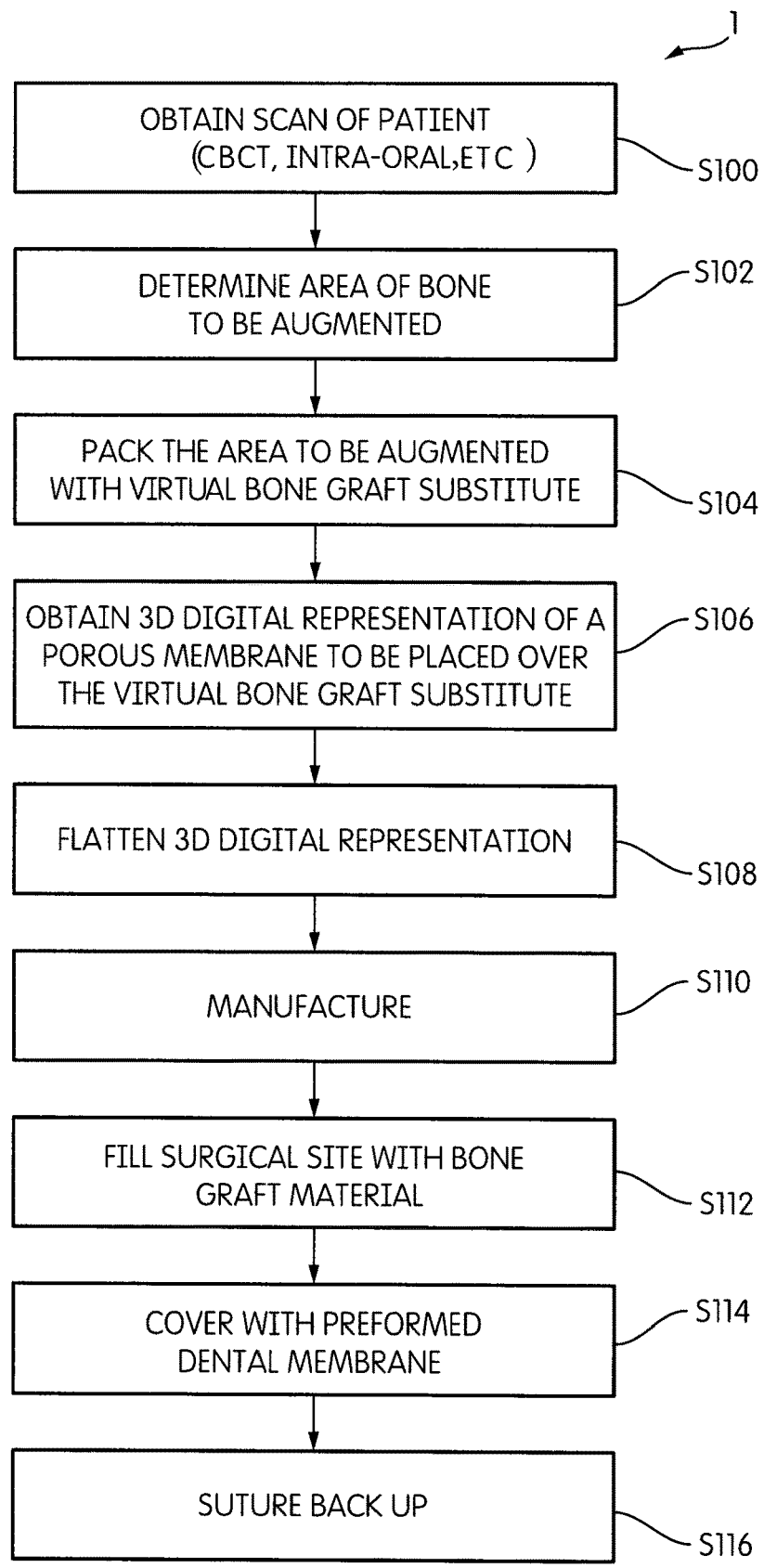
FIG. 3 illustrates a process according to an exemplary embodiment of the present invention.

FIG. 3 shows a process 1 of producing a physical preformed dental membrane. The process 1 may begin by obtaining a scan of a patient's dental cavity in Step S100. The scan may be a Cone Beam Computed Tomography (CBCT) scan, Magnetic Resonance Imaging (MRI) scan and/or intra-oral scan, said scan may include a surface topography of the surgical site 4. Herein, the scan may be obtained from a scanning step performed by the clinician. Alternatively, the clinician may obtain scan data from a previous scanning operation. If a CBCT scan is used, the exact bone quality, region of graft, and amount of graft required may be revealed.

After obtaining the scan, a rendering of the jaw 3 of the patient may be obtained based on the scan data and from said rendering of the jaw 3 (virtual jaw), an area of bone to be augmented, said area being a virtual representation of the surgical site 7, may be determined as shown in Step S102. In Step S104, the virtual representation of the surgical site 7 may be digitally packed with virtual bone graft material 18. Said digital packing may be based on one or more properties including bone quality, region of graft, and amount of graft, soft tissue topography and location of the proposed dental implant. The digital packing may show the volume of graft material needed. A main aim of the graft shape nay be to build up sufficient bone quantity to support a dental implant. The size of the dental implant may be based on the location of the implant. Smaller (3.0-4.0 mm) implants are normally placed in the anterior while larger 4.0+ mm implants are normally placed in the posterior. Ideally the graft site may have several mm of bone around the implant diameter to fully support osseointegration. Additionally, the graft site may match the neighboring dental anatomy in terms of ridge height and width.

Figure 4:
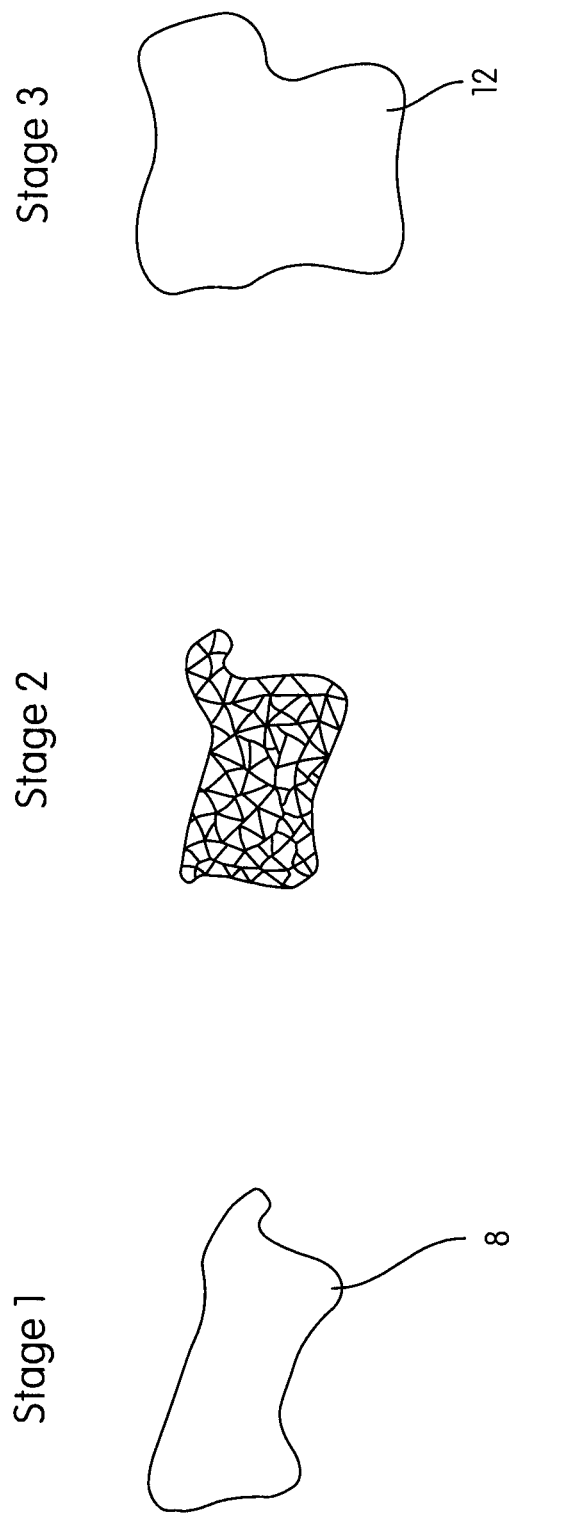

Subsequently, the virtual preformed membrane 6 to be placed over the virtual bone graft substitute 18 may be obtained in Step S106 by defining a three-dimensional geometry 8 of the virtual preformed membrane 6. The surface shape of the graft site may be obtained and isolated to create a virtual surface geometry of the graft site. This may then be used to create the custom membrane. This may be either a manual or automatic process. In an embodiment, a user or clinician can map out or mark the exact shape and desired coverage of the graft site. After defining the 3D geometry 8, the obtained virtual preformed dental membrane 6 may undergo a flattening process via meshing or via a similar algorithm (Step S108) as shown in Stage 2 of FIG. 4 to form a flat or substantially flat virtual sheet/virtual digital representation (showing the 2D contour of the flattened preformed dental membrane 6) of the preformed membrane 12. The flattening process can be accomplished by using CAD software that may pattern the 3D geometry into a flat 2D shape.

Once the virtual preformed dental membrane 6 is flattened, it may be manufactured, Step S110, and shaped at any point prior to dental treatment by the clinician. The manufacturing of this shape may be accomplished by creating a 3D printed structure of the augmented bone site and then overlaying a precut hydrated membrane over this form. Then the membrane may be dehydrated to hold its formed three-dimensional shape. Of course other methods including 3D printing of the membrane or using other molding or forming techniques may be realized. During dental treatment, the clinician may open up the augmentation site, pack the location with sufficient grafting material, and then place the membrane over to act as a barrier between the bone graft substitute and the soft tissue. Then the surgical site may be sutured and left to heal.

Preferably the manufactured preformed membrane may be made of collagen, non-resorbable polymers, resorbable polymers, synthetic resorbables, and/or natural resorbables.

During dental treatment, the physical surgical site 4 may be filled with actual bone graft material/substitute, Step S112 and covered with the shaped preformed dental membrane, Step S114. The surgical site 4 may then be sutured back up, Step S116.

Figure 5:
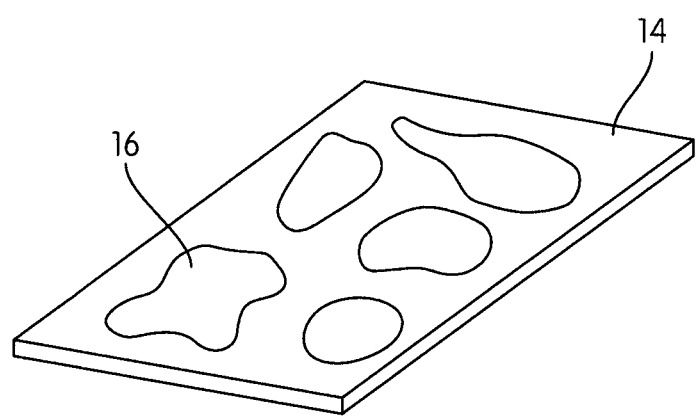
FIG. 5 illustrates a perspective view of an alternative embodiment of the present invention.
Figure 6:
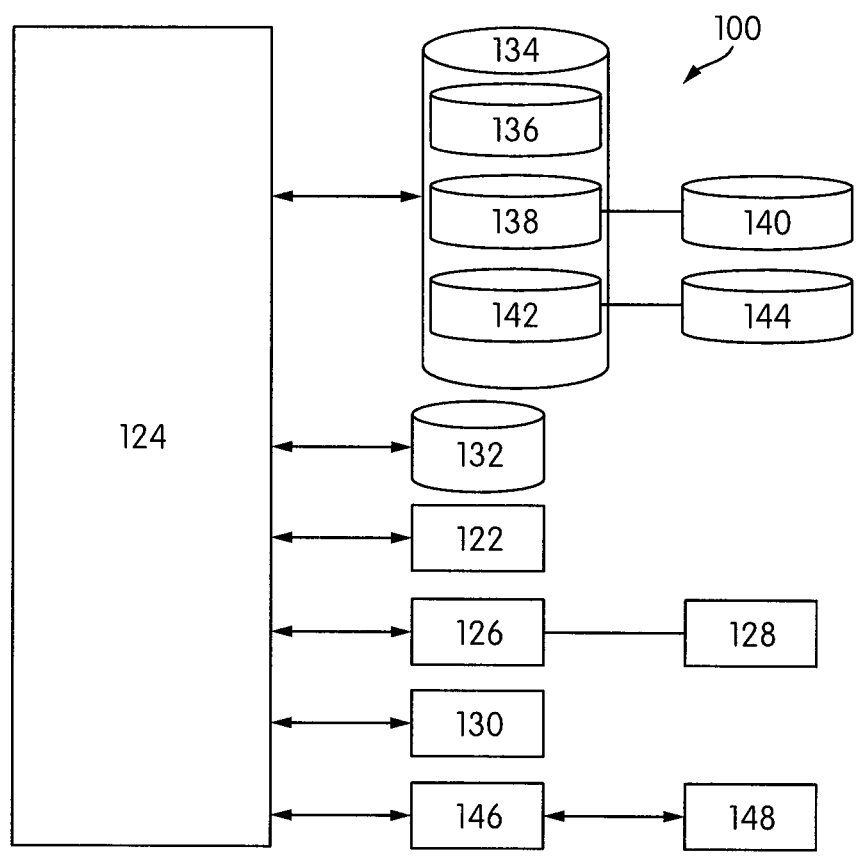
FIG. 6 illustrates a computer system according to an embodiment of the present invention.

FIG. 5 shows an alternative embodiment of the present invention. Herein, the virtual preformed membrane 6 may be configured into organic shapes that may be individually packed (for example, within its own separate sterile packaging for a single use device.), or be pre-cut into a larger membrane sheet 14. These geometries may not be specific for any one patient, but may represent standard membrane shapes that are most commonly used by clinicians. The clinician may benefit from this type of product by having a best fit alternative than requiring the need to hand modify a membrane shape during surgery. This may save time and provide a superior product during the bone grafting process. In this embodiment, a patient digital scan may not be required Computer System for Making a Custom Dental Membrane Having described a process 1 of making a custom dental membrane, reference will now be made to FIG. 6, which shows a block diagram of a computer system 100 that may be employed in accordance with at least some of the example embodiments herein. Although various embodiments may be described herein in terms of this exemplary computer system 100, after reading this description, it may become apparent to a person skilled in the relevant art(s) how to implement the disclosure using other computer systems and/or architectures.

The computer system 100 may include a scanner such as CBCT, MRI and/or intra-oral scanner for obtaining 3D images of the dental cavity. The computer system may also include at least one computer processor 122. The computer system may be configured to receive the 3D images and the processor 122 may be configured to analyze said 3D images in order to create the rendering of the jaw 3 which may be displayed on a display 128 of the computer system 100. In an embodiment herein the computer system 100 may take input from a clinician through an input unit such 130 such as a keyboard, mouse, touchscreen monitor or the like in order to create a finished preformed membrane 6. The input may include, among others, a selection of the boundaries of the surgical site, contour of bone structure, size of implant, location of implant, neighboring dental anatomy, critical nerves, existing bone, quality of bone, etc. In another embodiment, the processor 122 may be configured to automatically select the surgical site based on an analysis of the contour of bone, size of implant, location of implant, neighboring dental anatomy, critical nerves, existing bone, quality of bone, etc. The processor 122 may be connected to a communication infrastructure 124 (e.g., a communications bus, a cross-over bar device, or a network).

A display interface (or other output interface) 126 may forward video graphics, text, and other data from the communication infrastructure 124 (or from a frame buffer (not shown)) for display on the display unit 128.

One or more steps of creating the preformed membrane as shown in the process 1 of FIG. 3 may be stored on a non-transitory storage device in the form of computer-readable program instructions. To execute a procedure, the processor 122 loads the appropriate instructions, as stored on the storage device, into memory, and then executes the loaded instructions.

The computer system 100 may also comprise a main memory 132, which may be a random access memory ("RAM"), and also may include a secondary memory 134. The secondary memory 134 may include, for example, a hard disk drive 136 and/or a removable-storage drive 138 (e.g., a floppy disk drive, a magnetic tape drive, an optical disk drive, a flash memory drive, and the like). The removable-storage drive 138 may read from and/or write to a removable storage unit 140 in a well-known manner. The removable storage unit 140 may be, for example, a floppy disk, a magnetic tape, an optical disk, a flash memory device, and the like, which may be written to and read from by the removable-storage drive 138. The removable storage unit 140 may include a non-transitory computer-readable storage medium storing computer-executable software instructions and/or data.

In further alternative embodiments, the secondary memory 134 may include other computer-readable media storing computer-executable programs or other instructions to be loaded into the computer system 100. Such devices may include a removable storage unit 144 and an interface 142 (e.g., a program cartridge and a cartridge interface); a removable memory chip and an associated memory socket; and other removable storage units 144 and interfaces 142 that allow software and data to be transferred from the removable storage unit 144 to other parts of the computer system 100.

The computer system 100 also may include a communications interface 146 that enables software and data to be transferred between the computer system 100 and external devices. Software and data transferred via the communications interface 146 may be in the form of signals, which may be electronic, electromagnetic, optical or another type of signal that may be capable of being transmitted and/or received by the communications interface 146. Signals may be provided to the communications interface 146 via a communications path 148 (e.g., a channel). The communications path 148 may carry signals and may be implemented using wire or cable, fiber optics, a telephone line, a cellular link, a radio-frequency ("RF") link, or the like. The communications interface 146 may be used to transfer software or data or other information between the computer system 100 and a remote server or cloud-based storage (not shown).

One or more computer programs or computer control logic may be stored in the main memory 132 and/or the secondary memory 134. The computer programs may also be received via the communications interface 146. The computer programs may include computer-executable instructions which, when executed by the computer processor 122, cause the computer system 100 to perform the methods described. Accordingly, the computer programs may control the computer system 100.

In another embodiment, the software may be stored in a non-transitory computer-readable storage medium and loaded into the main memory 132 and/or the secondary memory 134 of the computer system 100 using the removable-storage drive 138, the hard disk drive 136, and/or the communications interface 146. Control logic (software), when executed by the processor 122, may cause the computer system 100, to perform all or some of the methods described herein.

Unless otherwise defined, all technical and scientific terms used herein have the same meaning as commonly understood by one of ordinary skill in the art to which this invention belongs. Although methods and materials similar to or equivalent to those described herein may be used in the practice or testing of the disclosure, suitable methods and materials are described above. All publications, patent applications, patents, and other references mentioned herein are incorporated by reference in their entirety to the extent allowed by applicable law and regulations. The disclosure may be embodied in other specific forms without departing from the spirit or essential attributes thereof, and it may therefore be desired that the present embodiment be considered in all respects as illustrative and not restrictive. Any headings utilized within the description are for convenience only and have no legal or limiting effect.

What is claimed is:

1. A method of making a preformed dental membrane, comprising the steps of:
   obtaining a virtual 3D image of an area of bone to be augmented, said area of bone to be augmented including a virtual representation of a surgical site;
   digitally packing the surgical site with virtual bone graft substitute;
   designing a virtual preformed dental membrane to be placed over the packed bone graft substitute based on the virtual bone graft substitute and the obtained virtual 3D image of the area of bone to be augmented; and
   fabricating a preformed dental membrane from the virtual preformed dental membrane by printing a 3D structure of the augmented bone site, overlaying a precut hydrated membrane over 3D structure, and dehydrating the precut hydrated membrane so that it holds its formed three-dimensional shape.

2. The method according to claim 1, wherein the virtual 3D image of the area of bone to be augmented is obtained from a CBCT, MRI and/or intraoral scan.

3. The method according to claim 1, wherein the digital packing step is based on one or more properties selected from the group consisting of bone quality, region of graft, amount of graft, soft tissue topography, size of a proposed dental implant and location of the proposed dental implant.

4. The method according to claim 1, further comprising;
   flattening the virtual preformed dental membrane into a substantially flat virtual sheet.

5. A method of using the preformed dental membrane of claim 1, further comprising physically packing the surgical site with bone graft substitute.

6. The method according to claim 5, further comprising:
   placing the fabricated preformed membrane over the packed bone graft substitute such that when said fabricated preformed membrane is placed over the packed bone graft substitute, its geometry conforms or substantially conforms to that of said virtual preformed dental membrane.

7. The method according to claim 1, wherein the virtual 3D image of the area of bone to be augmented is obtained from a previous scanning operation.

* * * * *